United States Patent
Yang et al.

(10) Patent No.: US 11,647,752 B2
(45) Date of Patent: May 16, 2023

(54) METHOD FOR CONTROLLING TOBACCO BACTERIAL WILT AND APPLICATION OF NAHS IN CONTROLLING TOBACCO BACTERIAL WILT

(71) Applicants: Hubei Institute of Tobacco Science, Wuhan (CN); Hubei University, Wuhan (CN)

(72) Inventors: Chunlei Yang, Wuhan (CN); Jun Yu, Wuhan (CN); Yong Yang, Wuhan (CN); Haibo Xiang, Wuhan (CN); Chunli Li, Wuhan (CN); Wan Zhao, Wuhan (CN); Jinpeng Yang, Wuhan (CN); Xiongfei Rao, Wuhan (CN); Shouwen Chen, Wuhan (CN)

(73) Assignees: Hubei Institute of Tobacco Science, Wuhan (CN); Hubei University, Wuhan (CN)

(*) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 17/536,104

(22) Filed: Nov. 29, 2021

(65) Prior Publication Data
US 2022/0167626 A1 Jun. 2, 2022

(30) Foreign Application Priority Data
Oct. 28, 2020 (CN) .......................... 202011171734.8

(51) Int. Cl.
 *A01N 63/20* (2020.01)
 *A24B 1/00* (2006.01)
 *C12N 1/20* (2006.01)
(52) U.S. Cl.
 CPC ................ *A01N 63/20* (2020.01); *A24B 1/00* (2013.01); *C12N 1/20* (2013.01)

(58) Field of Classification Search
None
See application file for complete search history.

(56) References Cited

FOREIGN PATENT DOCUMENTS

| | | | |
|---|---|---|---|
| AU | 2021100581 A4 * | 4/2021 | |
| CN | WO2008135093 A1 | 11/2008 | |
| CN | 104623705 A | 5/2015 | |
| CN | 105238876 A * | 1/2016 | ........... C12Q 1/6844 |
| CN | 106982624 A * | 7/2017 | |
| CN | 107137725 A | 9/2017 | |
| CN | WO2019129235 A1 | 7/2019 | |
| CN | 110521453 A * | 12/2019 | ......... A01G 13/0275 |

OTHER PUBLICATIONS

Zhang et al.(Effects of exogenous hydrogen sulfide on physiological and biochemical characteristics of tobacco seedlings under drought stress, Zhongguo Nongye Keji Daobao, 2018, 20(11), 112-119) . (Year: 2018).*
Li et al.(Acta Botanica Boreali-Occidentalia Sinica, 2019, vol. 39, No. 9, pp. 1609-1617, 37 refs.) (Year: 2019).*

* cited by examiner

*Primary Examiner* — Alton N Pryor

(57) ABSTRACT

A method for controlling tobacco bacterial wilt and an application of NaHS in controlling the tobacco bacterial wilt are provided by the present disclosure, and the disclosure belongs to the technical field of plant disease control. By measuring the growth effect of *Ralstonia solanacearum* in tobacco through plate and shake bottle experiments, the disclosure finds the NaHS has an inhibiting effect on the growth of the pathogen of bacterial wilt; and the influence of different concentration of NaHS on the incidence of bacterial wilt in tobacco is detected, and the result also shows that NaHS has a good effect on resisting bacterial wilt in tobacco. The disclosure finds and proves for the first time that NaHS is an effective antibacterial substance against bacterial wilt and provides a new method for prevention and controlling of the tobacco bacterial wilt.

1 Claim, 11 Drawing Sheets
Specification includes a Sequence Listing.

SEQUENCE LISTING

<160> NUMBER OF SEQ ID NOS: 18

<210> SEQ ID NO 1
<211> LENGTH: 21
<212> TYPE: DNA
<213> ORGANISM: Artificial Sequence
<220> FEATURE:
<223> OTHER INFORMATION: Synthesized

<400> SEQUENCE: 1
gtcgccgtca actcactttc c                                              21

<210> SEQ ID NO 2
<211> LENGTH: 24
<212> TYPE: DNA
<213> ORGANISM: Artificial Sequence
<220> FEATURE:
<223> OTHER INFORMATION: Synthesized

<400> SEQUENCE: 2
gtcgccgtca gcaatgcgga atcg                                           24

<210> SEQ ID NO 3
<211> LENGTH: 20
<212> TYPE: DNA
<213> ORGANISM: Artificial Sequence
<220> FEATURE:
<223> OTHER INFORMATION: Synthesized

<400> SEQUENCE: 3
agagtttgat cctggctcag                                                20

<210> SEQ ID NO 4
<211> LENGTH: 22
<212> TYPE: DNA
<213> ORGANISM: Artificial Sequence
<220> FEATURE:
<223> OTHER INFORMATION: Synthesized

<400> SEQUENCE: 4
tacggttacc ttgttacgac tt                                             22

<210> SEQ ID NO 5
<211> LENGTH: 19
<212> TYPE: DNA
<213> ORGANISM: Artificial Sequence
<220> FEATURE:
<223> OTHER INFORMATION: Synthesized

<400> SEQUENCE: 5
gtgccagcmg ccgcggtaa                                                 19

<210> SEQ ID NO 6
<211> LENGTH: 20
<212> TYPE: DNA
<213> ORGANISM: Artificial Sequence
<220> FEATURE:
<223> OTHER INFORMATION: Synthesized

<400> SEQUENCE: 6
ggactachvg ggtwtctaat                                                20

<210> SEQ ID NO 7
<211> LENGTH: 22
<212> TYPE: DNA
<213> ORGANISM: Artificial Sequence

```
<220> FEATURE:
<223> OTHER INFORMATION: Synthesized

<400> SEQUENCE: 7
ggaagtaaaa gtcgtaacaa gg                                          22

<210> SEQ ID NO 8
<211> LENGTH: 20
<212> TYPE: DNA
<213> ORGANISM: Artificial Sequence
<220> FEATURE:
<223> OTHER INFORMATION: Synthesized

<400> SEQUENCE: 8
gctgcgttct tcatcgatgc                                             20

<210> SEQ ID NO 9
<211> LENGTH: 23
<212> TYPE: DNA
<213> ORGANISM: Artificial Sequence
<220> FEATURE:
<223> OTHER INFORMATION: Synthesized

<400> SEQUENCE: 9
gacaaaggga cattacaaga agt                                         23

<210> SEQ ID NO 10
<211> LENGTH: 20
<212> TYPE: DNA
<213> ORGANISM: Artificial Sequence
<220> FEATURE:
<223> OTHER INFORMATION: Synthesized

<400> SEQUENCE: 10
gagaaggatt atgccaccag                                             20

<210> SEQ ID NO 11
<211> LENGTH: 20
<212> TYPE: DNA
<213> ORGANISM: Artificial Sequence
<220> FEATURE:
<223> OTHER INFORMATION: Synthesized

<400> SEQUENCE: 11
aacctttgac ctgggacgac                                             20

<210> SEQ ID NO 12
<211> LENGTH: 20
<212> TYPE: DNA
<213> ORGANISM: Artificial Sequence
<220> FEATURE:
<223> OTHER INFORMATION: Synthesized

<400> SEQUENCE: 12
gcacatccaa cacgaaccga                                             20

<210> SEQ ID NO 13
<211> LENGTH: 18
<212> TYPE: DNA
<213> ORGANISM: Artificial Sequence
<220> FEATURE:
<223> OTHER INFORMATION: Synthesized

<400> SEQUENCE: 13
ttctcggagc ctcttatg                                               18
```

```
<210> SEQ ID NO 14
<211> LENGTH: 17
<212> TYPE: DNA
<213> ORGANISM: Artificial Sequence
<220> FEATURE:
<223> OTHER INFORMATION: Synthesized

<400> SEQUENCE: 14
ccctcttccc accttgc                                              17

<210> SEQ ID NO 15
<211> LENGTH: 17
<212> TYPE: DNA
<213> ORGANISM: Artificial Sequence
<220> FEATURE:
<223> OTHER INFORMATION: Synthesized

<400> SEQUENCE: 15
tcacccgtgg tattagg                                              17

<210> SEQ ID NO 16
<211> LENGTH: 18
<212> TYPE: DNA
<213> ORGANISM: Artificial Sequence
<220> FEATURE:
<223> OTHER INFORMATION: Synthesized

<400> SEQUENCE: 16
gttcctgtag gacaagca                                             18

<210> SEQ ID NO 17
<211> LENGTH: 22
<212> TYPE: DNA
<213> ORGANISM: Artificial Sequence
<220> FEATURE:
<223> OTHER INFORMATION: Synthesized

<400> SEQUENCE: 17
gccgactaca acatccagaa gg                                        22

<210> SEQ ID NO 18
<211> LENGTH: 21
<212> TYPE: DNA
<213> ORGANISM: Artificial Sequence
<220> FEATURE:
<223> OTHER INFORMATION: Synthesized

<400> SEQUENCE: 18
tgcaacacag cgagcttaac c                                         21
```

METHOD FOR CONTROLLING TOBACCO BACTERIAL WILT AND APPLICATION OF NAHS IN CONTROLLING TOBACCO BACTERIAL WILT

CROSS-REFERENCE TO RELATED APPLICATIONS

The application claims priority to Chinese patent application No. 202011171734.8, filed on Oct. 28, 2020, the entire contents of which are incorporated herein by reference.

TECHNICAL FIELD

The present disclosure belongs to the technical field of plant disease control, in particular to a method for controlling tobacco bacterial wilt and an application of the NaHS in controlling the tobacco bacterial wilt.

BACKGROUND

*Ralstonia solanacearum* is an important soil-borne pathogen with a wide host range, which can infect more than 450 species of plants in more than 50 families, causing serious losses to many crops and cash crops. *Ralstonia solanacearum* is one of the main diseases that restrict tobacco production in China, which brings great economic losses to tobacco industry every year. At present, tobacco bacterial wilt is prevalent in the Yangtze River valley and the tobacco growing areas to the south of China, causing serious harm. The investigation of tobacco diseases and insect pests in 16 provinces of China in 2008 showed that the damaged area of *Ralstonia solanacearum* reached 50 000 $hm^2$, resulting in a yield reduction of about 7.6393 million kg and an economic loss of up to 115.2215 million yuan. Once the tobacco plants in the field were infected with bacterial wilt, the diseased plants would wither and die rapidly with the favorable conditions of high temperature and humidity.

A great deal of hard work has been done to control bacterial wilt. Previous studies have focused on the use of planting systems and organic fertilizers to control tobacco bacterial wilt, but there are no specific methods to treat tobacco bacterial wilt worldwide.

Hydrogen sulfide, a colorless, flammable and smelly egg-smelling gas, has long been considered as a hazard to the growth and development of animals and plants. However, recent studies have shown that $H_2S$ is another novel endogenous gas signaling molecule after NO and CO in organisms. In humans and animals, $H_2S$ is involved in the physiological and pathological processes such as vasodilation, lowering blood pressure, mediating inflammation, protecting cells and protecting cardiovascular system. Although the biological role of $H_2S$ in plants has been reported, the understanding of the mechanism of $H_2S$ regulating plant growth and development is far from clear compared with the understanding of its role in animals. It has been pointed out that $H_2S$ is involved in many aspects of plant is involved in many aspects of plant growth and development, as well as its resistance to external stress, including the effects of $H_2S$ on plant suspension cell activity, stomatal opening, lateral root germination and plant stress resistance.

SUMMARY

In view of the problems existing in the prior art, the present disclosure provides a method for controlling tobacco bacterial wilt and an application of the NaHS in controlling the tobacco bacterial wilt, with the aim of solving some problems in the prior art or at least alleviating some problems in the prior art.

The disclosure is implemented in this way: a method for controlling tobacco bacterial wilt, comprising: adding NaHS to a culture medium.

The present disclosure further provides an application of the NaHS in controlling the tobacco bacterial wilt.

The present disclosure further provides an application of the NaHS in a preparation of a bacteriostatic reagent of *Ralstonia solanacearum*.

The present disclosure further provides an application of the NaHS in regulating transcription of anti-*Ralstonia solanacearum* related genes in tobacco.

Further, the present disclosure provides the application of the NaHS in the regulating transcription of the anti-*Ralstonia solanacearum* related genes in the tobacco, wherein the anti-*Ralstonia solanacearum* related genes in the tobacco comprises one or more of NtACC Oxidase, NtPR1a/c, E3ligase and Thaumatin.

The present disclosure further provides an application of the NaHS in regulating bacterial and/or fungal diversity in soil.

Further, the present disclosure provides the application of the NaHS in regulating the bacterial and/or the fungal diversity in the soil, wherein: the NaHS increases richness of antagonistic bacteria of verrucomicrobia, bacteroides and phylum firmicutes, and richness of antagonistic bacteria of basidiomycota and chytridiomycota in fungal phylum in phylum microorganism of tobacco rhizosphere soil.

Further, the present disclosure provides the application of the NaHS in regulating the bacterial and/or the fungal diversity in the soil, wherein: the NaHS reduces abundance of tobacco harmful bacteria of acidobacteria in the bacterial phylum and abundance of tobacco harmful bacteria of ascomycota in the fungal phylum.

In summary, the advantages and positive effects of the present disclosure are:

the control of tobacco bacterial wilt with $H_2S$ or its donor has not been reported. Therefore, the research of $H_2S$ enhancing tobacco disease resistance production practice will be helpful to further understand the role of this new type of gas signal molecule, in order to provide theoretical and practical basis for the development and utilization of $H_2S$ and the promotion of tobacco bacterial wilt control. The disclosure finds and proves for the first time that the $H_2S$ exogenous additive NaHS is an effective bacteriostatic substance against the bacterial wilt pathogen, and provides a new method for controlling the bacterial wilt of tobacco.

DETAILED DESCRIPTION OF THE EMBODIMENTS

Figure 1:
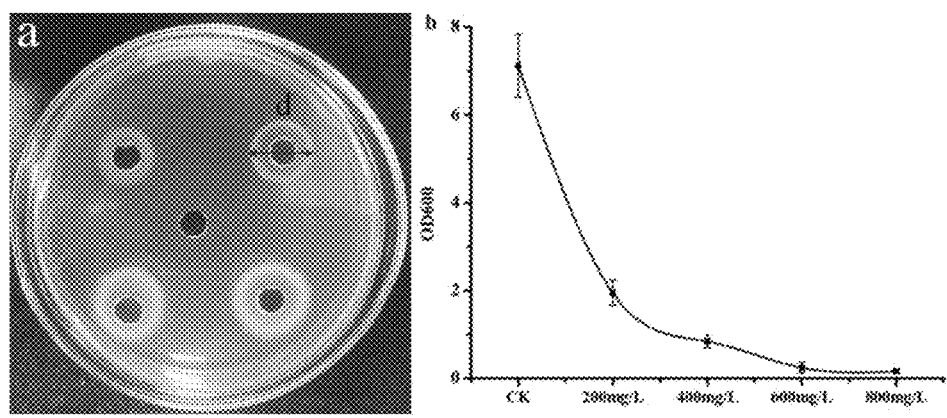
FIG. 1 shows inhibitory effect of different concentrations of NaHS on tobacco bacterial wilt; wherein: a shows the inhibition of different concentrations of NaHS on the growth of *Ralstonia solanacearum*; 1:200 mg/L; 3:0 mg/L; 2:400 mg/L; 5:800 mg/L; b shows the effect of different concentrations of NaHS on the biomass of *Ralstonia solanacearum*.

In order to make the object, technical solution and advantages of the present disclosure more clear, the present disclosure is described in further detail below in connection with the embodiments, and the equipment and reagents used in each of the embodiments and test examples can be obtained from a commercial way unless otherwise specified. The specific embodiments described herein are only intended to explain the disclosure and are not intended to limit the disclosure.

According to the information contained in the present application, it is easy for those skilled in the art to make various changes to the precise description of the disclosure without departing from the spirit and scope of the appended claims. It should be understood that the scope of the disclosure is not limited to the processes, properties, or components defined, as these embodiments and other descriptions are merely illustrative of specific aspects of the disclosure. In fact, it is apparent to those skilled in the art or related art that various changes that can be made to embodiments of the disclosure are covered by the appended claims.

In order to better understand that present disclosure and not limit the scope of the present disclosure, all of the figures used in the present application, in all cases it shall be understood to be qualified by the word "approximately". Therefore, unless otherwise specified, the numerical parameters set forth in the description and the appended claims are approximate, which may vary depending on the desired nature sought. Each numerical parameter shall at least be considered to be obtained from the reported significant figures and by conventional rounding. In that present disclosure, "about" refer to within 10% of a given value or range, preferably within 5%.

The disclosure provides a method for controlling tobacco bacterial wilt and an application of the NaHS in controlling the tobacco bacterial wilt, and specific embodiments are as follows.

Embodiment

1. The disclosure relates to the cultivation of tobacco seedlings: the tested flue-cured tobacco variety is Yunyan 87, and the seeds of the Yunyan 87 are provided by Hubei Tobacco Company. Sowing: 2~3 seeds are sown on each plug tray in the seedling tray. Incubation conditions: the room temperature is controlled at 28±2° C. day and night, and the relative humidity is controlled above 80%.

The test strain: *Ralstonia solanacearum* tobacco is deposited by the research team.

NA medium: beef extract 3 g, yeast powder 1 g, peptone 5 g, and glucose 10 g, add distilled water to constant volume to 1000 mL.

MS Medium:

| MS Medium composition (unit: mg/L) | |
|---|---|
| Composition | Content |
| $NH_4NO_3$ | 1650 |
| $CaCl_2$ | 332.2 |
| $MgSO_4$ | 180.7 |
| $KNO_3$ | 1900 |
| $KH_2PO_4$ | 127.5 |
| $K_2HPO_4$ | 42.5 |
| $H_3BO_3$ | 6.2 |
| $CoCl_2 \cdot 6H_2O$ | 0.025 |
| $CuSO_4 \cdot 5H_2O$ | 0.025 |
| FeNaEDTA | 36.7 |
| $MnSO_4 \cdot H_2O$ | 16.9 |
| $Na_2MoO_4 \cdot 2H_2O$ | 0.25 |
| KI | 0.83 |
| $ZnSO_4 \cdot 7H_2O$ | 8.6 |
| Glycine | 2 |
| moy-Inositol | 100 |
| Nicotinic acid | 0.5 |
| Pyridoxine HCL | 0.5 |
| Thiamine HCL | 0.1 |
| Sucrose | 30000 |
| Agar | 6060 |

2. Determination of Inhibitory Effect on Growth of *Ralstonia solanacearum*

Five treatments are set in the experiment, i.e., NaHS concentrations of 0 mg/L, 200 mg/L, 400 mg/L, 600 mg/L and 800 mg/L, respectively.

Plate Confrontation Method:

heating and dissolving the sterilized NA solid medium completely, cooling to about 55° C., pouring it into the culture dish with 15 mL for each dish, and setting it for use after solidification; evenly coating the bacterial suspension of *Ralstonia solanacearum* with a concentration of $1.0 \times 10^8$ CFU %/mL on the plate surface with a coating rod; drilling Four holes with a diameter of 5 mm on the NA medium with a diameter of 90 mm by the drilling method; and adding 50 μL NaHS solution with different concentrations into the holes. After air drying, placing the plate in the incubator at 37° C., checking the bacteriostatic effect after 12 h, measuring the diameter of the bacteriostatic ring with the cross method, and recording the size of the bacteriostatic ring.

Shake Flask Culture Method:

adding 30 mL NA medium into 250 mL volumetric flask, inoculating 600 μL bacterial suspension of tobacco bacterial wilt at $1.0 \times 10^8$ CFU mL/mL after sterilization, and adding 1 mL NaHS solution of different concentrations, shaking culture for 12 h at 37° C. and 230 r/m, and determining the $OD_{600}$ value of bacterial biomass after centrifugation and dilution of fermentation liquid.

Experimental Results:

in order to investigate whether NaHS has an inhibitory effect on the growth of tobacco bacterial wilt, effect of NaHS on the growth of tobacco bacterial wilt is studied in 5 treatment groups (CK, N200, N400, N600 and N800). The results show that the diameter of inhibition zone of N200-N800 is 11.20±0.72, 14.61±0.93, 19.43±0.41, 21.21±1.22 mm respectively. The results showed that NaHS have inhibitory effect on the growth of tobacco bacterial wilt pathogen HF-1-1, and the inhibitory effect of NaHS on bacterial wilt pathogen increased with the increase of concentration. When the concentration of exogenous NaHS is 800 mg/L, the inhibitory effect on HF-1-1 is the most significant (FIG. 1A, Table 1). In addition, by adding different concentrations of NaHS (0, 200, 400, 600, 800 mg/L) to the liquid culture of HF-1-1, it is found that the biomass of the pathogen HF-1-1 decreased with the increase of its concentration, which further confirmed that NaHS has an inhibitory effect on the growth of the pathogen *Ralstonia solanacearum* (FIG. 1B). At the same time, the results also showed for the first time that NaHS is an effective antibacterial substance against bacterial wilt.

TABLE 1

Inhibitory Ring Diameter of Different Concentrations of NaHS on the Growth of Tobacco Bacterial Wilt

| Processing | 0 mg/L | 200 mg/L | 400 mg/L | 600 mg/L | 800 mg/L |
|---|---|---|---|---|---|
| Diameter of inhibition zone (mm) | 9.00 + 0.00 d | 11.20 ± 0.72 c | 14.61 ± 0.93 b | 19.43 ± 0.41 a | 21.21 ± 1.22 a |

3. Study on the Growth of *Ralstonia solanacearum* in Tobacco Root:

using the method of MS medium hydroponics, adding 50 mL ½ MS liquid medium into the tissue culture bottle, washing the root substrate of the three-leafed and one-heart tobacco seedling, fixing the tobacco seedling with a sponge, soaking the root in the culture medium, adding a proper amount of culture medium every day, replacing the culture medium once every 3 days, after culturing for 3 days, adding 10 mL 0.8 mmol hydroxylamine as $H_2S$ inhibitor respectively; the concentration of 200 mg/L, 400 mg/L, 600 mg/L and 800 mg/L NaHS solution as $H_2S$ exogenous donor, 10 ml water as control, and setting six treatments for the test. Inoculating three-leafed and one-heart tobacco root irrigation of different treatments grown on MS medium with 10 ML of *Ralstonia solanacearum* suspension with a concentration of $1.0 \times 10^8$ CFU mL/mL. At 12 h, 24 h and 36 h after inoculation, removing the aboveground parts, washing with sterile water and drying the root surface water with absorbent paper, then weighing and recording. Soaking the tobacco root in 75% ethanol for 15 min, then rinsing it with distilled water for 5-6 times, absorbing the water and putting it in a sterilized mortar, adding 5 mL sterile water, grinding it fully, standing for 5 min, and then absorbing 1 mL of supernatant liquid, then obtaining the suspension of bacteria in the tobacco root. Diluting the root bacterial suspension by 10-fold gradient, and taking 100 μL suspension with appropriate concentration to evenly coat on a solid TTC plate, and culturing the suspension at 37° C. for 12 h, and then carrying out the bacterial identification and colony count, calculating the content of *Ralstonia solanacearum* in the root of tobacco under unit weight. The test is repeated for three times.

Figure 2A:
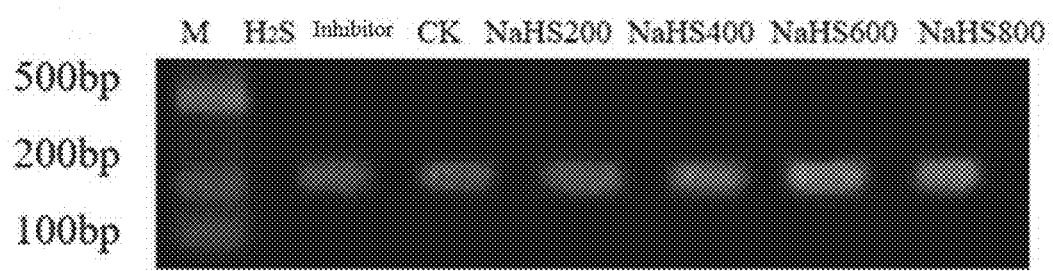
FIG. 2A and FIG. 2B show colonization of *Ralstonia solanacearum* in tobacco roots by different concentrations of NaHS; wherein: a shows identification of *Ralstonia solanacearum* in tobacco roots; b shows effects of different concentrations of NaHS on the colonization of *Ralstonia solanacearum* in tobacco roots.
Figure 2B:
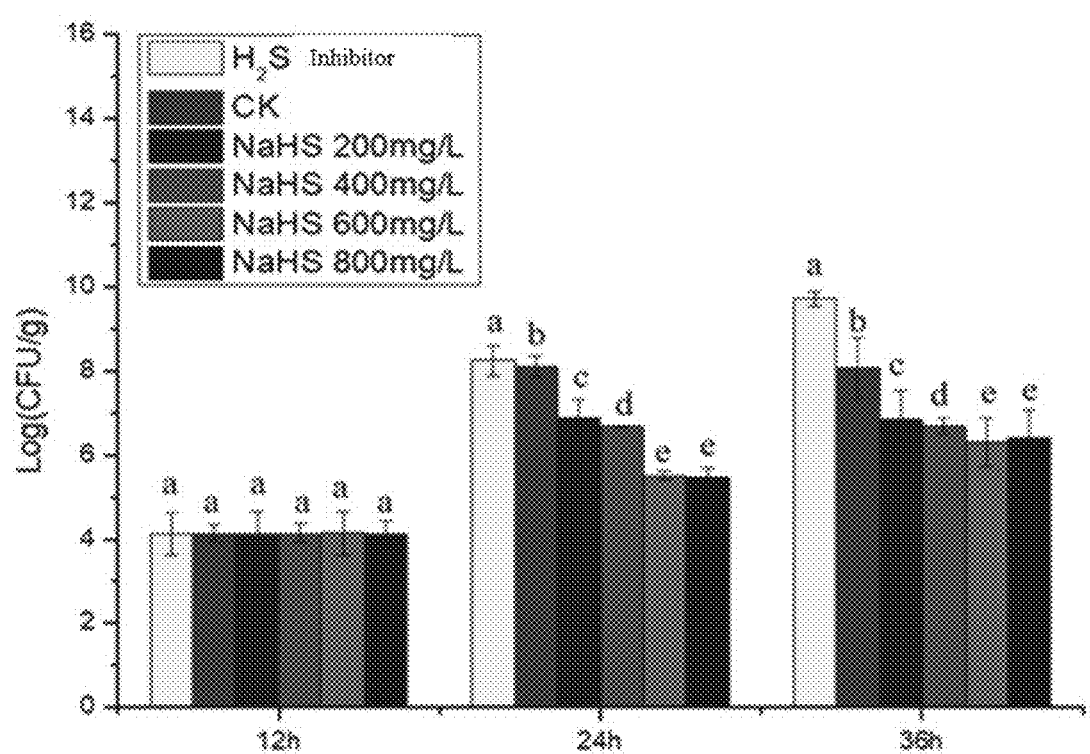

Experimental Results:

first, the tobacco plants were treated with different concentrations of NaHS (0, 200, 400, 600, 800 mg/L) and $H_2S$ inhibitor. Then, tobacco plants of 6 treatment groups (CK, N-, N200, N400, N600 and N800) are inoculated with *Ralstonia solanacearum* and cultured. Next, the early-cultured tobacco root bacteria are identified, and PCR verification is carried out using *Ralstonia solanacearum* 16S RNA characteristic primers (see the method below), and it is found that the tobacco root bacteria contained *Ralstonia solanacearum* (FIG. 2A). Finally, the colonization of *Ralstonia solanacearum* on tobacco roots is determined and counted. The results show that at 12 h of inoculation, the amount of *Ralstonia solanacearum* in the roots treated with CK-N800 is $1.36 \times 10^4$ CFU/g, $1.38 \times 10^4$ CFU/g, $1.36 \times 10^4$ CFU/g, $1.39 \times 10^4$ CFU/g, 1.40, respectively $\times 10^4$ CFU/g, $1.37 \times 10^4$ CFU/g, there is no significant difference between different treatment samples. At 24 h and 36 h, although the content of *Ralstonia solanacearum* in the tobacco roots increased, compared with the CK and N-treatment groups, the content of *Ralstonia solanacearum* in the tobacco roots treated with N200-N800 is relatively lower, and with the increase of NaHS concentration, the number of *Ralstonia solanacearum* colonizing tobacco roots gradually decreases. Among them, the addition of 800 mg/L NaHS has the most significant effect. Compared with the control group, the number of *Ralstonia solanacearum* colonized on tobacco roots decreased by 98.32% at 36 hours (FIG. 2B). In summary, these results show that the exogenous addition of NaHS can effectively inhibit the growth of *Ralstonia solanacearum*, thereby significantly inhibiting the colonization of *Ralstonia solanacearum* in tobacco roots, thereby greatly reducing the pathogenicity rate of *Ralstonia solanacearum* to tobacco.

4. Identification of *Ralstonia solanacearum*:

specific primers identified *Ralstonia solanacearum*:

*Ralstonia solanacearum* specific primer 759/760 is used for PCR amplification. The primer is synthesized by Wuhan Qingke Innovation Biotechnology Co., Ltd. and the primer sequence is: 759: 5'-GTCGCCGTCAACTCACTTTCC-3', SEQ ID NO.1, 760: 5'-GTCGCCGTCAGCAATGCG-GAATCG-3', SEQ ID NO.2. 25 μL reaction system is used for PCR amplification, and the reaction solution included: 10×PCR Buffer 2.5 4, 25 mM $MgCl_2$ 2 μL, 2.5 mM dNTP 1 μL, 5 U Taq, enzyme 0.2 μL, 1 μL of 2.5 μMol/L primer 759 and 1 μL of 25 μMol/L primer 760, the template DNA 50 ng, ddH2O is supplemented with 25 μL and amplified on the mycycler@PCR amplification apparatus of Bio-Rad Company.

The PCR procedure is as follows: the first step is 95° C. pre-denaturation for 2 min, the second step is 94° C. denaturation for 20 s, 68° C. annealing for 20 s, 72° C. extension for 30 s, and the third step is 72° C. extension for 10 min. 54 PCR products are electrophoresed in 2% agarose gel at a voltage of 5 V/cm. The Biorad gel imager is used to observe the results and to determine whether the strain is *Ralstonia solanacearum* according to the PCR amplification.

16S rRNA Sequence Analysis of *Ralstonia solanacearum*:

five strains are randomly selected from all isolates for 16S rRNA sequence analysis. The PCR amplification is performed with the bacterial 16S rRNA universal primers 27f and 1492r, and the primer sequence is as follows: 27f: 5'-AGAGTTTGA TCCTGGCTCAG-3', SEQ ID NO.3, 1492r: 5'-TACGGTTACCTTGTTACGACTT-3', SEQ ID NO.4.

50 μL reaction system is used for PCR amplification, and the reaction solution included 10×PCR Buffer 5 μL, 25 mM MgCl24 μL, 2.5 mM dNTP 5 U Taq enzyme 0.4 μL, 25 μmol/L primer 27f and 1492r 2 μL, respectively, and the template DNA 50 ng, ddH2O is supplemented with 50 μL and amplified on the mycycler@PCR amplification apparatus of Bio-Rad Company.

The PCR procedure is as follows: the first step is 96° C. pre-denaturation for 5 min, the second step is 94° C. denaturation for 1 min, 50° C. annealing for 1 min, 72° C. extension for 30 min, 30 cycles in total, and the third step is 72° C. extension for 10 min. The PCR amplification products are recovered and sequenced by Wuhan Qingke Innovation Biotechnology Co., Ltd. The sequences are sequenced in NCBI for BLAST homology search and comparison.

5. Statistical Analysis on Occurrence of Tobacco Bacterial Wilt

After transplanting tobacco seedlings for 7 days, the pathogen of bacterial wilt is inoculated. After 65 days, the occurrence of tobacco bacterial wilt in each treatment is investigated and analyzed according to the industrial standard GB/T23222-2008 Classification and Investigation Method of Tobacco Diseases and Pests [S]. Beijing: China Standard Press, 2008.].

Classification Criteria of Tobacco Bacterial Wilt:
grade 0: disease-free;
grade 1: stems occasionally have chlorotic spots, or leaves below half of the diseased side are withered;
grade 3: black stripe on the stem, but not more than half of the stem height, or half to two-thirds of the leaf wilting on the diseased side;
grade 5: black stripe on the stem is more than half of the height of the stem, but does not reach the top of the stem, or more than two-thirds of the leaf wilting on the diseased side;
grade 7: the black stripe on the stem reaches the top of the stem, or all the leaves of the diseased plant wilts;
grade 9: basically withered.

Statistical analysis: The incidence, disease index and relative control effect of each treatment were statistically analyzed by SPSS 18.0 software. Disease index and control effect calculation formula:

$$Incidence = \frac{Number\ of\ diseased\ plants}{Total\ number\ of\ plants} \times 100\%$$

$$Disease\ index = \frac{\sum \left( \begin{array}{c} Disease\ representative\ value \times \\ Number\ of\ diseased\ plants\ of\ the\ disease\ grade \end{array} \right)}{Representative\ value\ of\ highest\ disease\ grade \times Total\ number\ of\ plants\ surveyed} \times 100\%$$

$$Relative\ control\ effect = \frac{CK_2\ Disease\ index \times Treatment\ condition\ index}{CK_2\ Disease\ index} \times 100\%$$

Experimental Results:

in order to investigate the effect of exogenous addition of NaHS on the incidence of tobacco bacterial wilt, 5 different concentrations of NaHS (0, 200, 400, 600, 800 mg/L) are added to tobacco seedlings in this example, and the 5 treatment groups are named as CK, N200, N400, N600 and N800 respectively. The tobacco seedlings are transplanted for 7 days and then inoculated with bacterial wilt pathogen. Finally, the occurrence of tobacco bacterial wilt in different concentration of NaHS treatment group is analyzed after 65 days (Table 2). It is found that the incidence and disease index of tobacco treated with different concentrations of NaHS are significantly lower than those of the control group, and with the increase of NaHS concentration, the incidence and disease index decrease gradually. In addition, according to the disease index, the control effect of each treatment group is calculated. It is found that the relative control effect of N800 treatment is the highest (89.50%), followed by N600 treatment (82.99%). The results show that NaHS has a good effect on tobacco resistance to bacterial wilt, and NaHS could significantly improve the control effect of tobacco soil-borne diseases.

TABLE 2

Effects of Different Concentrations of NaHS on the Incidence and Disease Index of Tobacco Bacterial Wilt

| Processing Group | Incidence | Disease index | Relative control effect % |
|---|---|---|---|
| CK 0 mg/L | 90.67% a | 40.56 a | / |
| NaHS 200 mg/L | 44.00% b | 13.20 b | 67.46% a |
| NaHS 400 mg/L | 29.33% c | 8.76 c | 78.40% b |
| NaHS 600 mg/L | 20.67% d | 6.90 d | 82.99% c |
| NaHS 800 mg/L | 15.33% e | 4.26 e | 89.50% d |

6. Measurement of Transcription Level of Tobacco Resistance Gene to Bacterial Wilt Based on RT-PCR, the response of tobacco resistance gene to *Ralstonia solanacearum* infection in different concentrations of NaHS is investigated. Four specific resistance genes: NtACC Oxidase, NtPR1a/c, E3ligase and Thaumatin, are selected to analyze the expression of related genes.

One day after inoculation, three plants are taken from each of the six treatments, and 0.1 g of root in the same part of each plant is quickly transferred to the 1.5 mL RNase-free centrifuge tube, after frozen in liquid nitrogen and stored at −80° C., total RNA is extracted from plant tissues by Trizol method. 1 µL total RNA in each sample is used for reverse transcription. The reverse transcription reaction is performed according to the instructions of kit (iScript™ cDNA Synthesis Kit). The product cDNA is stored at −80° C. for future use. Primers used in the test (see Table 3):

TABLE 3

Primers used in the test

| Primer Name | Primer sequence (5'-3') |
|---|---|
| NtACCOxidaseF | GACAAAGGGACATTACAAGAAGT, SEQ ID NO. 9 |
| NtACCOxidaseR | GAGAAGGATTATGCCACCAG, SEQ ID NO. 10 |
| NtPR1a/cF | AACCTTTGACCTGGGACGAC, SEQ ID NO. 11 |
| NtPR1a/cR | GCACATCCAACACGAACCGA, SEQ ID NO. 12 |
| E3ligaseF | TTCTCGGAGCCTCTTATG, SEQ ID NO. 13 |
| E3ligaseR | CCCTCTTCCCACCTTGC, SEQ ID NO. 14 |
| ThaumatinF | TCACCCGTGGTATTAGG, SEQ ID NO. 15 |

TABLE 3-continued

Primers used in the test

| Primer Name | Primer sequence (5'-3') |
|---|---|
| ThaumatinR | GTTCCTGTAGGACAAGCA, SEQ ID NO. 16 |
| UBI3F | GCCGACTACAACATCCAGAAGG, SEQ ID NO. 17 |
| UBI3R | TGCAACACAGCGAGCTTAACC, SEQ ID NO. 18 |

The UBI3 gene is selected as the internal reference gene based on tobacco resistance to bacterial wilt. PCR amplification: the reaction system is 20 μL, including 10 μL SYBR, 1 μL upstream and 1 μL downstream primers and 1 μL cDNA L, 7 μL ddH2O. The samples are mixed in a tube and put into a 96-well PCR plate, then put into a real-time fluorescence quantitative PCR instrument for PCR amplification. The reaction procedure is as follows: 95° C. pre-denaturation for 3 min; the cycle conditions are 95° C. 10 s, 54° C. 20 s, a total of 40 cycles.

Experimental Results:

effects of different concentrations of NaHS on the expression of tobacco resistance genes to bacterial wilt;

four specific resistance genes based on tobacco bacterial wilt resistance transcriptome sequencing were selected in this example: NtACC Oxidase, NtPR1a/c, E3ligase and Thaumatin are studied. Six tobacco groups (N-, CK, N200, N400, N600 and N800) are treated with RT-qPCR, and the transcription of the four genes is analyzed.

Figure 3:
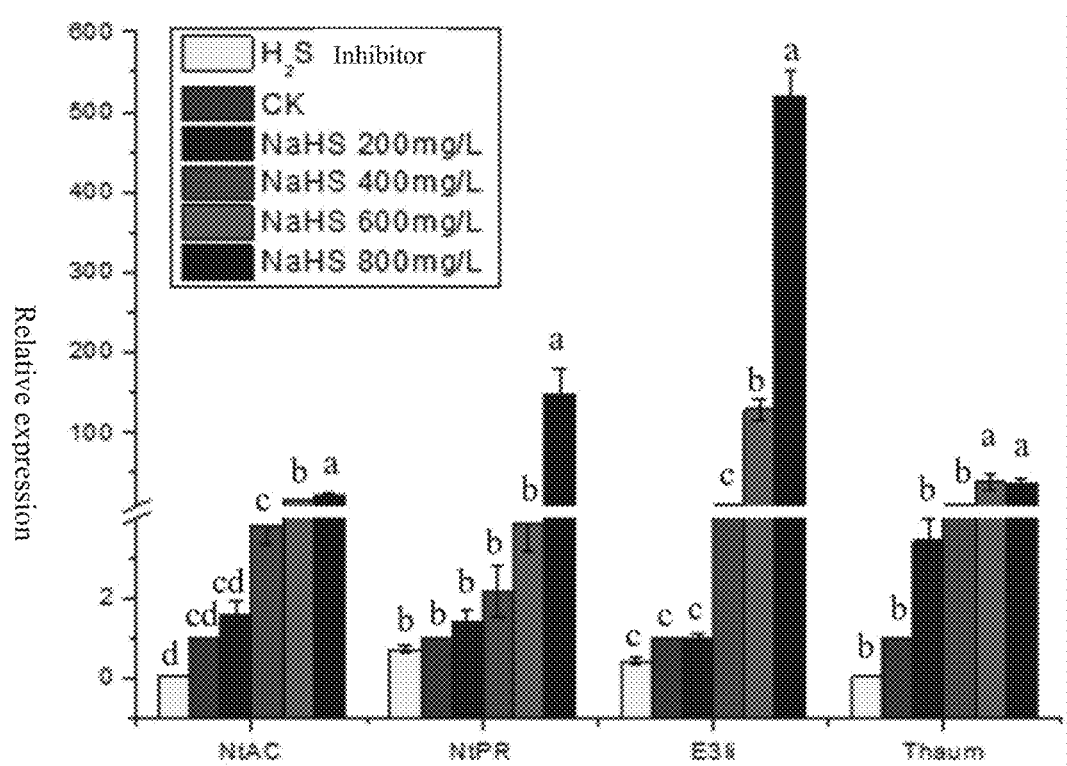
FIG. 3 shows effects of different concentrations of NaHS on the expression of tobacco resistance genes to bacterial wilt.

The results show that, compared with CK, the transcriptional expression of four resistance-related genes in tobacco plants treated with N200-N800, and the NtACC Oxidase of ethylene pathway-related genes increase by 1.59, 3.83, 15.83 and 22.99 times respectively. The relative expression level of salicylic acid pathway related genes NtPR1a/c is up-regulated by 1.42, 2.16, 3.86 and 148.84 times, respectively. At the same time, we find that the transcription of E3 ligase-related gene E3 ligase of N800 treatment is upregulated 520.87 times, while the upregulation of the other three genes is also significant, indicating that the resistance of tobacco is the strongest under the NaHS treatment of 800 mg/L, which is the most suitable for the growth of tobacco seedlings could improve the resistance of tobacco plants (FIG. 3). The results are consistent with the above experimental results, indicating that exogenous NaHS could up-regulate the transcription of genes related to bacterial wilt resistance in tobacco plants, thus increasing the resistance of tobacco to bacterial wilt, and reducing the pathogenicity of bacterial wilt to tobacco.

7. Collection of Rhizosphere Soil Samples of Tobacco Plants:

in 2018, rhizosphere soil samples were collected 100 days after transplanting. The rhizosphere soil of 5 tobacco plants was collected in each plot and mixed into one sample. There were 15 Soil samples in total. After the soil sample is evenly mixed, the debris such as stone grains and plant residues were removed, and the soil sample were brought back to the laboratory in dry ice; and after returning to the laboratory, store the soil sample in −80° C. refrigerator for DNA extraction.

8. Diversity Analysis of Soil Microbial Community:

8.1 DNA Extraction and PCR Amplification:

total soil DNA was extracted according to FastDNA Spin Kit kit (MP Biomedicals, USA).

515F (5'-GTGCCAGCMGCCGCGGTAA-3', SEQ ID NO.5) and 806R (5'-GGACTACHVGGGTWTCTAAT-3', SEQ ID NO.6) primers were used to amplify the bacterial 16S rDNA V4 variable region. The ITS1 region of fungi was amplified by PCR ITS5-1737F (5'-GGAAGTAAAAGTCGTAACAAGG-3', SEQ ID NO.7) and ITS2-2043R (5'-GCTGCGTTCTTCATCGATGC-3', SEQ ID NO.8). The amplification system was 304, including 15 μL Phusion Master Mix Buffer (2×), 34 primer (2 μM), 10 μL DNA (1 ng/μL) template and 2 μL H2O. The reaction procedure was: 98° C. 1 min; 98° C. 10 s, 50° C. 30 s, 72° C. 30 s (30 cycles); 72° C. 5 min (Bio-rad T100 gradient PCR instrument). The PCR product was qualified by 2% agarose gel electrophoresis, then the library was constructed, and the Illumina Hiseq PE250 sequencing platform was used for computer sequencing (Nuohe Zhiyuan Biological Information Technology Co., Ltd.).

8.2 Data Analysis:

the original raw tags are obtained by splicing the data from the lower machine, after strict filtering and removing the chimera sequence, effective tags are obtained, which is the effective data for subsequent analysis. Effective tags of all samples are clustered by using Uparse software (Uparse v7.0.1001), and the sequences are clustered into OTUs (Operational Taxonomic Units) with 97% identity. Species annotation of OTUs is carried out, and bacterial species annotation analysis is carried out by using Mothur method and SSU rRNA database of SILVA (http://www.arb-silva.de/) to obtain the community composition at each classification level; fungal species annotation analysis is carried out by using blast method in Qime software (Version 1.9.1) and Unit database (set threshold value as E-value=10-5) to obtain the community composition at each classification level.

8.3 Data Analysis:

rarefaction analysis is done by using motherr software, and dilution curve is drawn by using perl language tool. Sobs and Chao 1 richness index, and Shannon diversity index are calculated by Mothur software, and the sequencing depth was expressed by coverage. According to the species annotation and abundance information of the samples at the genus level, the abundance is standardized to obtain the Z value, and the heatmap is drawn by Hemi software. Where Z is the difference between the relative abundance of the samples in the classification and the average relative abundance of all samples in the classification divided by the standard deviation of all samples in the classification. Based on the relative abundance of each species at the phylum and genus classification level, the One-way Anova in SPSS22.0 software is used to analyze the variance to reflect the difference among the treatments. When $P<0.05$, the difference is considered to be significant.

Figure 4:
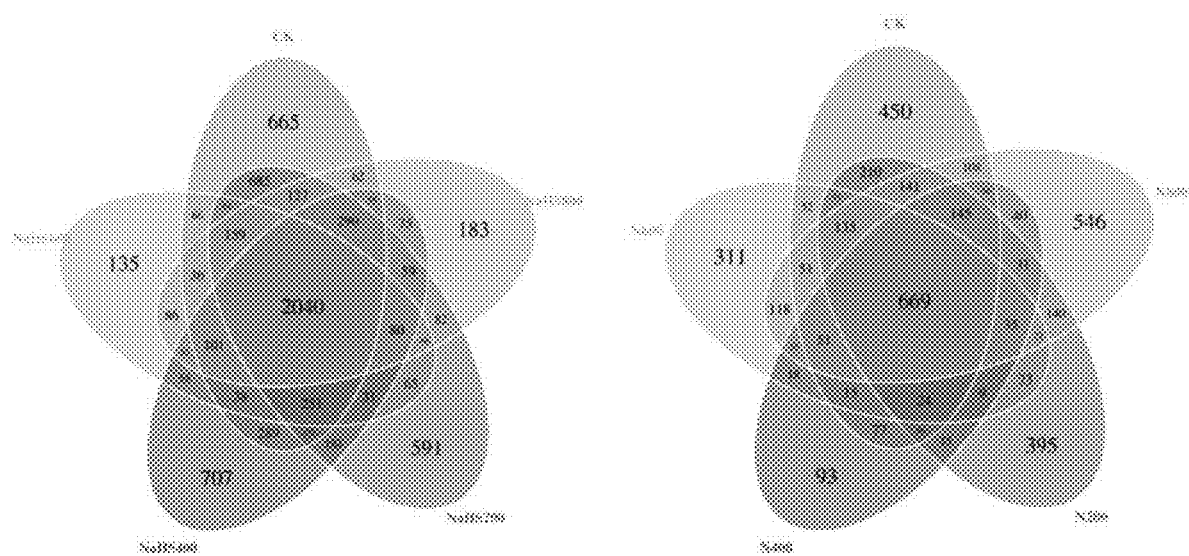
FIG. 4 shows effects of different concentration of NaHS on microecology of tobacco soil.
Figure 5A:
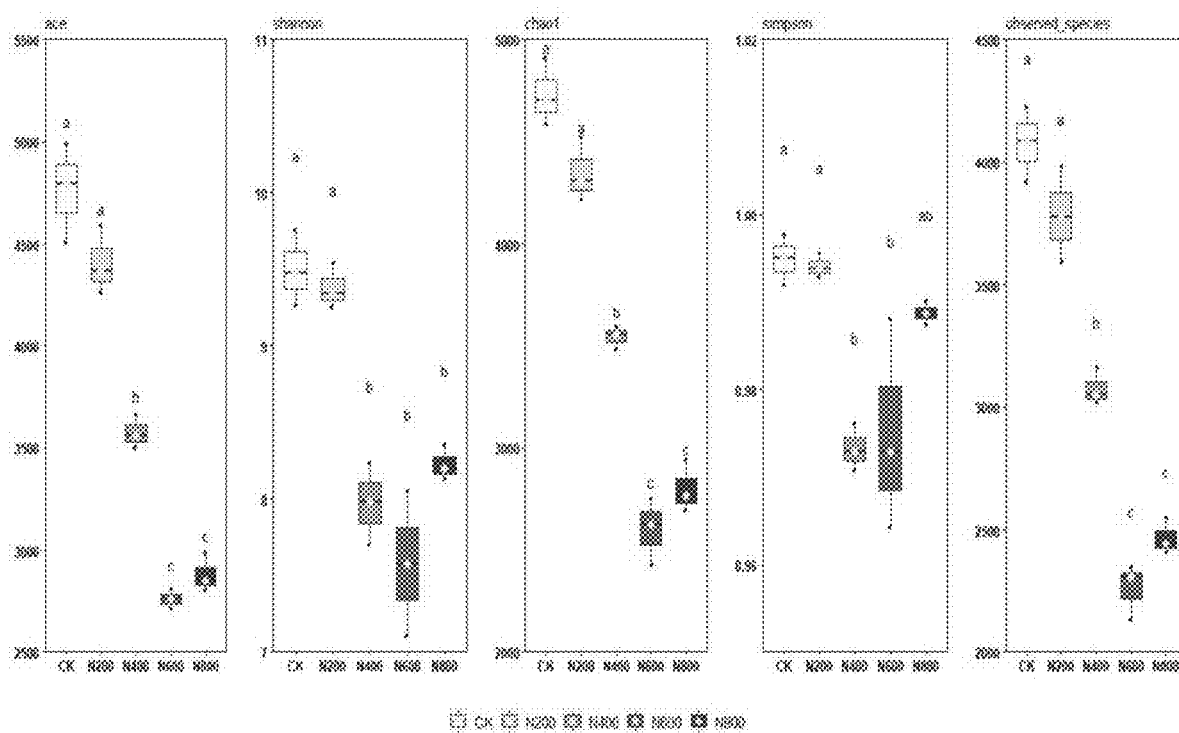
FIG. 5A and FIG. 5B show effects of different concentrations of NaHS on tobacco soil microecology simpson index map.
Figure 5B:
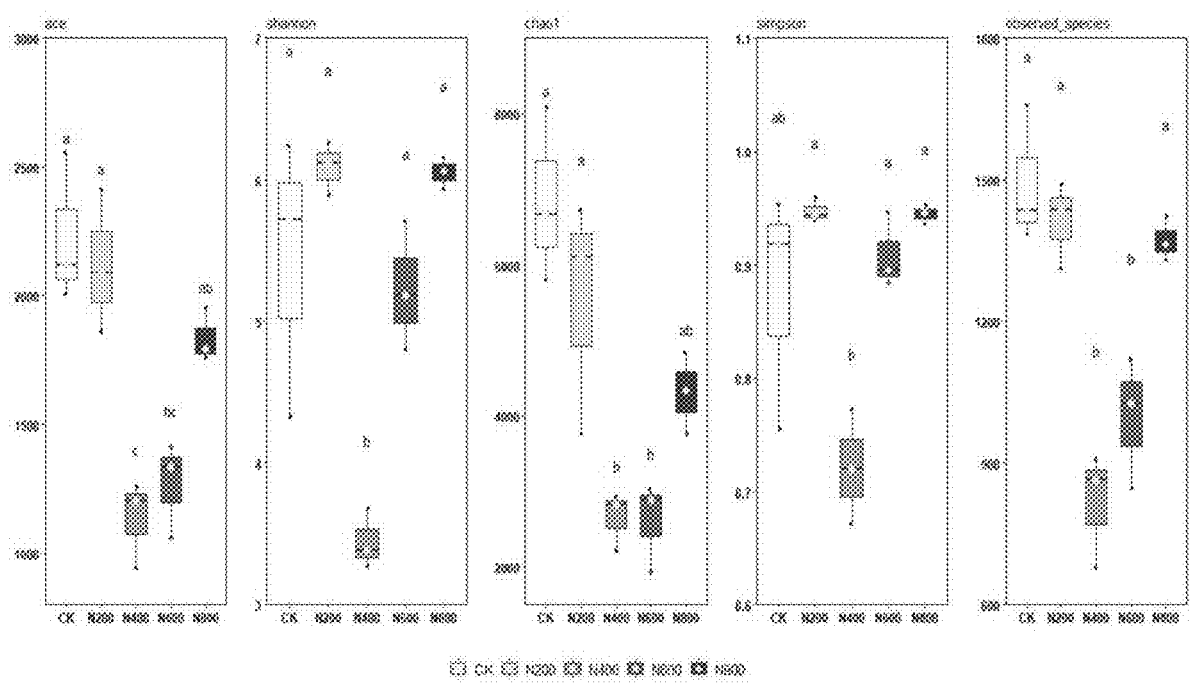

Experimental Results:

1) Effects of Different Concentrations of NaHS on Diversity of Bacteria and Fungi in Soil the embodiment explors the effects of different concentrations of NaHS on tobacco soil microecology. First, we analyze the effects of different concentrations of NaHS on bacterial and fungal diversity in tobacco soil, and identify 4201 fungal OTUs (operational taxonomic units, based on 99.5% identity) and 8204 bacterial OTUs in tobacco soil samples treated with 5 treatment groups (CK, N200, N400, N600 and N800) (FIG. 4). The diversity and abundance of bacterial and fungal communities are analyzed by one-way ANOVA. The results show that there are significant differences in soil bacterial community Observed species, Shannon, Ace, Simpson and Chao1 indexes among the treatment groups, the Observed species index, Shannon index, Ace index and Chao1 index of N400-N800 are significantly lower than those of the control group. In addition, the Simpson index shows only a significant difference between N600 and CK, no significant difference between N200 and N400 and CK, and no significant difference between N800 and CK (FIG. 5A). However, the Observed species, Shannon, Ace and Simpson indices of soil fungi community are significantly lower than those of the other treatments (N400=22.08~74.69%, 51.72~76.66%, 11.86~96.17% and 21.40~31.49%). The Chao Chao1 index is lower in N600 than that in other treatment groups. There are significant differences between N400, N600 and control group, but the change between N400 and N600 is 1.61%, there is no significant difference. To sum up, the results show that the application of NaHS has a certain effect on the diversity and abundance of bacteria and fungi community in rhizosphere soil of tobacco plants, and there are differences according to the concentration of NaHS. The concentration of NaHS is 400 mg/L (N400) and 600 mg/L (N400) respectively. (FIG. 5B)

2) Analysis of Relative Abundance of Soil Microbial Phylum:

based on the above results, the top 10 organisms in relative abundance of tobacco rhizosphere soil in 5 treatment groups (CK, N200, N400, N600, N800) are analyzed. The results show that the abundance of proteobacteria is the highest (40.26%~50.68%) among the three groups, while the other phyla are verrucomicrobia (3.34%~16.23%), bacteroidetes (6.11%~12.49%), firmicutes (1%~13.93%) and cyanobacteria (1.08~5.90%), gemmatimonadetes (3.52~6.91%), acidobacteri (3.24~6.20%), actinobacteria (2.10~5.23%), saccharibacteria (1.22~2.35%), and chloroflexi (1.12~3.21%). The relative abundance of these 10 phyla is 94.38~97.17%.

Figure 6A:
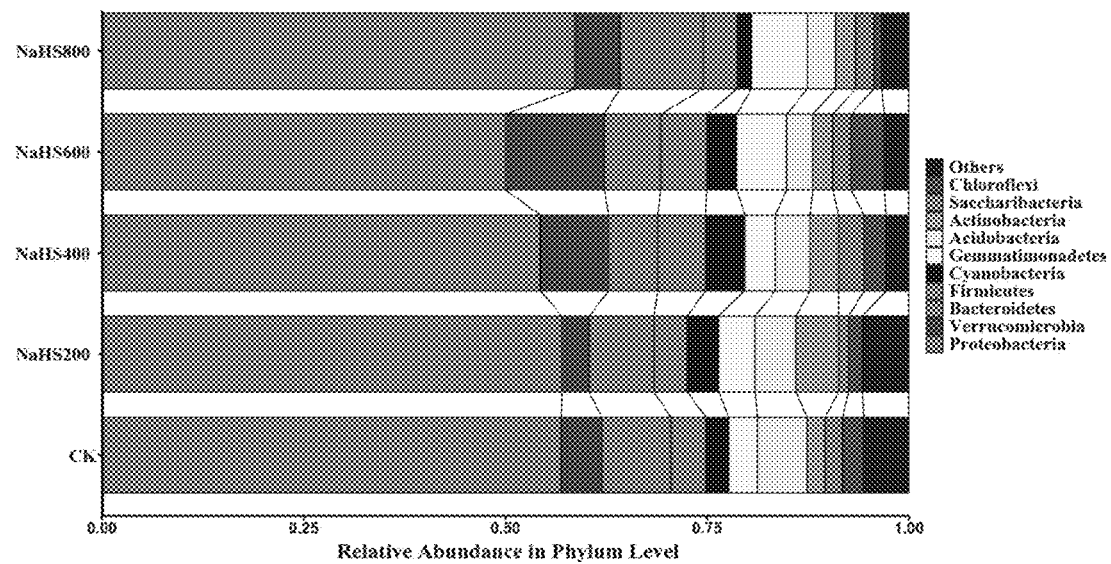
FIG. 6A and FIG. 6B show analysis on relative abundance of different concentration of NaHS on soil microbial phylum.

In addition, among these 10 bacterial phyla, the relative abundances of verrucomicrobia, bacteroidetes and firmicutes are significantly different from those of the control. Among them, the relative abundance of gemmatimonadetes in N200-N800 treatment groups increases by 6.57%-96.10%;

in the N600 treatment, the relative abundance of verrucomicrobia and bacteroidetes increases by 223.77% and 45.43%, respectively; in the N400 treatment, the relative abundance of firmicutes is significantly higher than that in the other treatments, with an increase range of 220.69-558.21%. In the other groups, there is no significant difference between CK and N800, but there is significant difference between CK and N200-N600 (FIG. 6A).

Figure 6B:
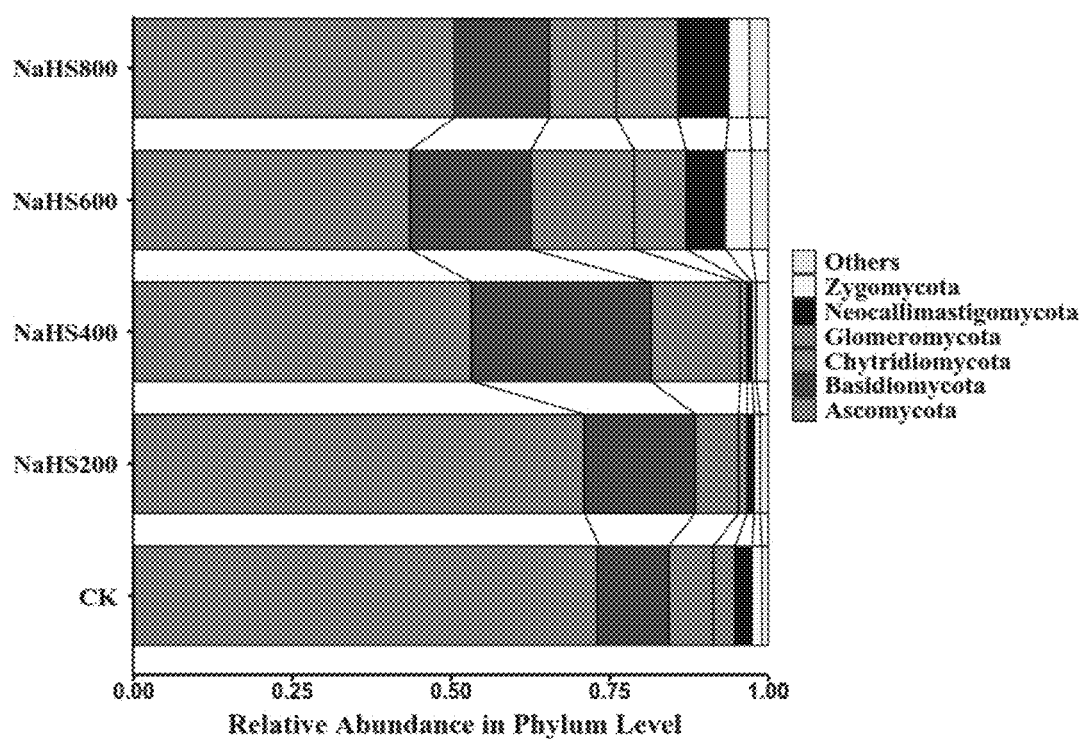

In that phylum trichoderma, the proportion of ascomycota, chytridiomycota, zygomycota, basidiomycetes, glomeromycota and neocallimastigomycota are 33.56-73.48%, 6.83-60.25%, 0.09-10.66%, 3.31-18.47%, 0.03-1.42% and 0.00-0.1%, respectively. In addition, the relative abundance of basidiomycetes in N200, N400 and N600 is significantly different from that of the control, which are 51.22%, 268.72% and 53.05%, respectively. However, in the chytridiomycota, the N400 and N600 are significantly higher than those in the control group, with an increase of 504.13% and 202.18%, respectively. However, in ascomycota, N400 treatment is significantly lower than the control group, the decrease is 54.43%; there is no significant difference between the treatments and the control in the phyla (FIG. 6B). According to the results, we speculate that one of the reasons for NaHS to improve the resistance of tobacco to *Ralstonia solanacearum* is that the NaHS increases richness of antagonistic bacteria of verrucomicrobia, bacteroides and phylum firmicutes, and richness of antagonistic bacteria of basidiomycota and chytridiomycota in fungal phylum in phylum microorganism of tobacco rhizosphere soil, thereby improving the growth environment of tobacco and greatly reducing the incidence of *Ralstonia solanacearum*, and reducing the richness of harmful bacteria in tobacco of acidobacteria in bacteria and ascomycota in fungi is reduced, and improving the growth environment of tobacco, so that the incidence of bacterial wilt is greatly reduced.

Figure 7A:
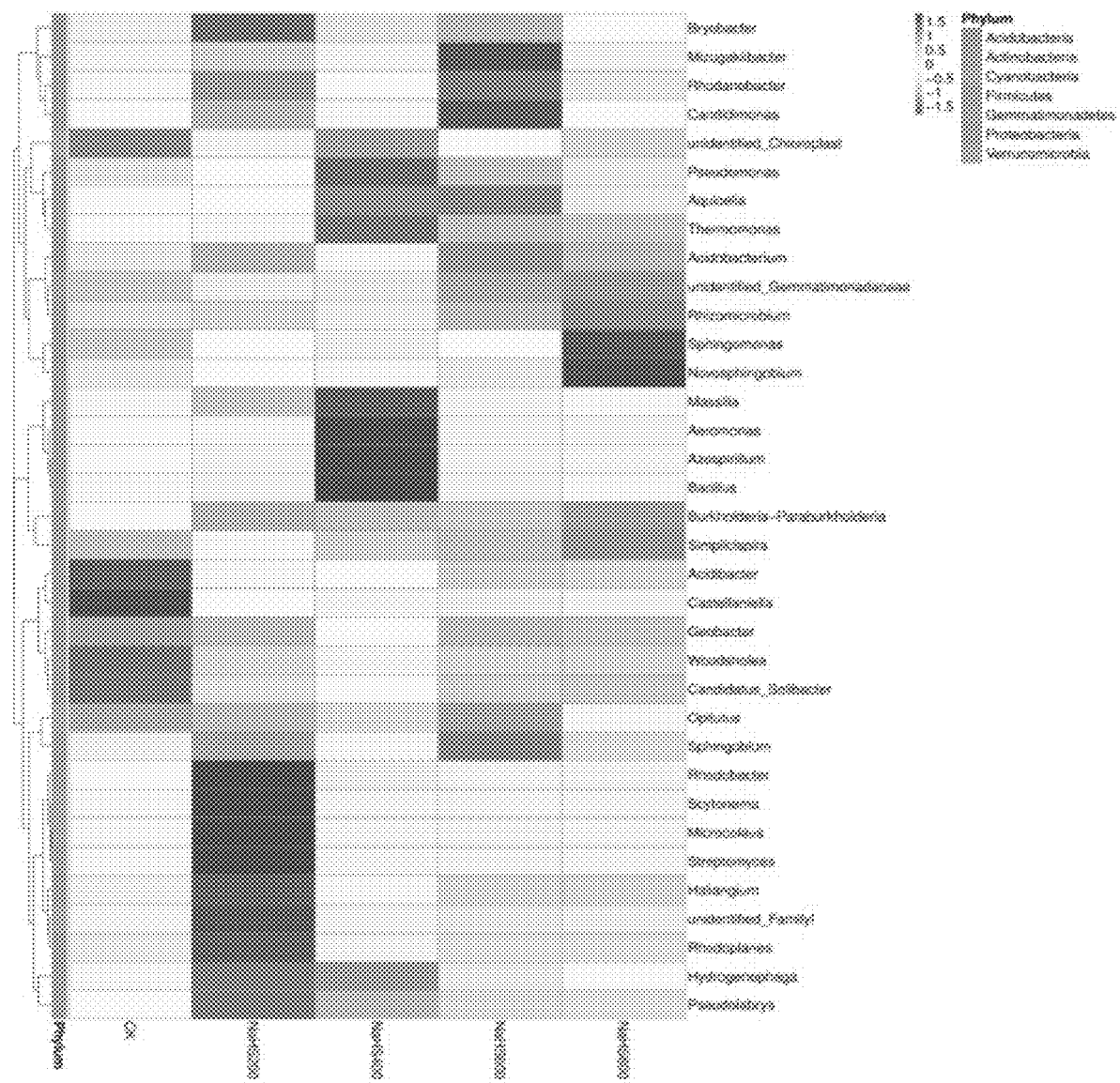
FIG. 7A and FIG. 7B show analysis of composition of dominant microorganisms in functional genera of soil with different concentrations of NaHS.
Figure 7B:
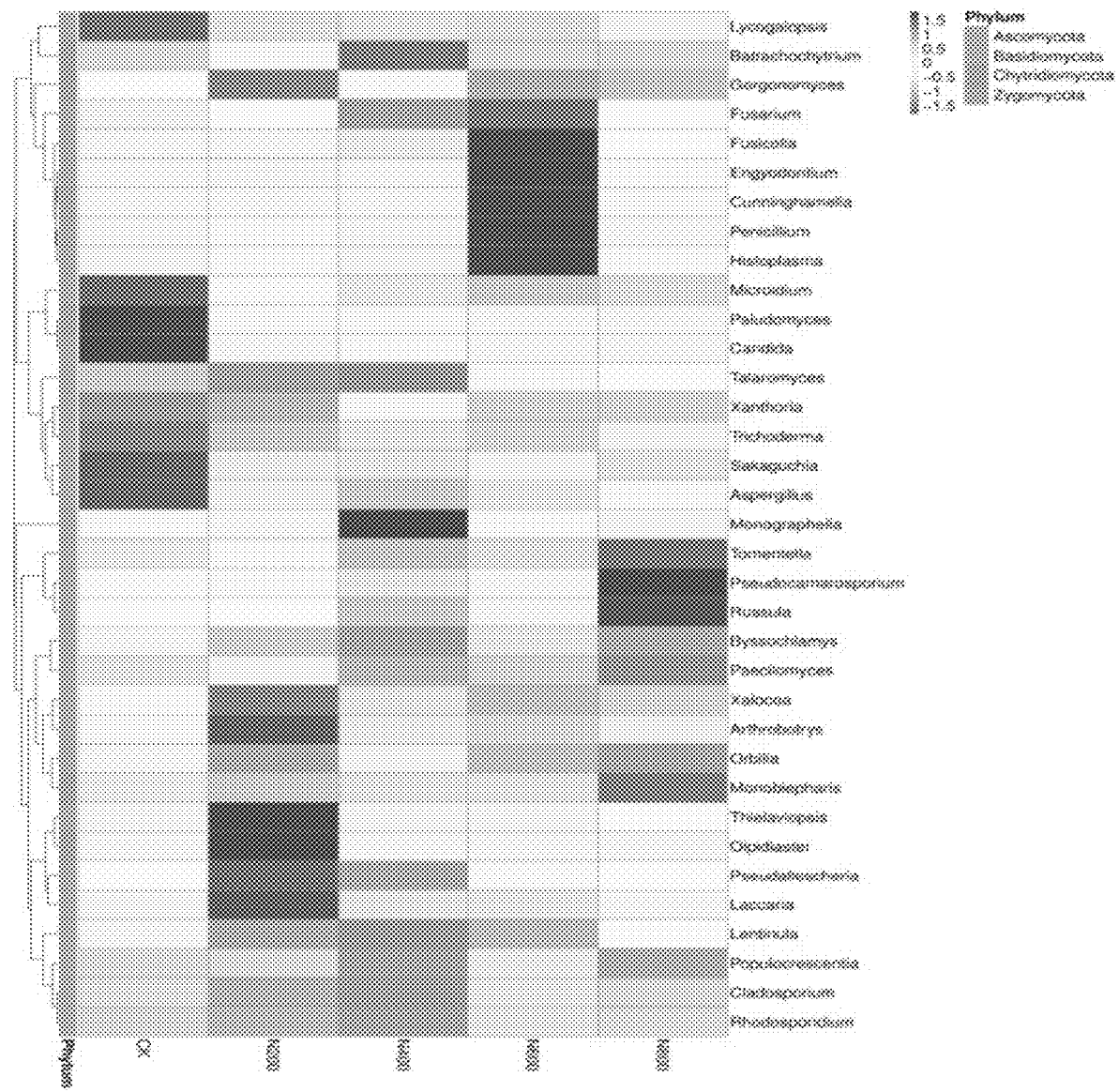

3) Composition Analysis of Dominant Microorganisms at Functional Genus Level:

subsequently, we analyze the relative abundance of 35 bacterial functional microorganisms and 35 fungal functional microorganisms in tobacco rhizosphere soil with promotion of tobacco plant growth and antagonism to *Ralstonia solanacearum*, and plot Heatmap to analyze the abundance variation of these bacterial microorganisms (FIG. 7A) and fungal microorganisms (FIG. 7B) in different treatments. The results show that the N600 and N800 treatment groups have similar abundance composition among the bacterial functional microorganisms, and gathered into one group, of which 13 and 17 functional microorganisms had higher relative abundance in the N600 and N800 treatment groups, while the N200 treatment group was grouped into one group. Among them, *Rhodobacter, Scytonema, Microcoleus* and *Streptomyces* are relatively abundant; the abundance of *Massillia, Aeromonas, Azospirillum* and *Bacillus* is significantly higher than that of other functional microorganisms in the same group, and 5 functional microorganisms in the control group have higher relative abundance (FIG. 7A). Among the fungal microorganisms, N400 is a self-contained species, and the relative abundance of *Monographella* microorganism is significantly higher than that of other microorganisms. The composition of N200 and the composition of N800 are similar, *Monoblepharis* and the abundance of 6 kinds of fungi such as *Orbilia* is higher, but each of them has its own microbial, *Thielaviopsis* with higher abundance and 4 kinds of fungi such as *Olpidiaster* has higher abundance in N200 treatment group, and the abundance of 3 kinds of fungi such as, *Tomentella* and *Pseudocamarosporium* is higher in N800 treatment group. In the N600 group, the abundance of *Fusicolla, Engyodontium* and other 6 species of fungi and microorganisms is high, but the similarity with other groups is low (FIG. 7B).

The above is only a preferred embodiment of the present disclosure and is not intended to limit the present disclosure, and any modifications, equivalent substitutions, improvements, etc. made within the spirit and principles of the present disclosure should be included within the scope of protection of the present disclosure.

What is claimed is:

1. A method of applying sodium hydrogen sulfide, NaHS, to a tobacco plant in upregulating transcription of anti-*ralstonia solanacearum*-resistant related genes in the tobacco plant for improving bacterial wilt resistance in the tobacco plant; wherein the NaHS is applied in a concentration of 200 mg/L, 400 mg/L, 600 mg/L, or 800 mg/L; and the anti-*ralstonia solanacearum* related genes comprise at least one of NtACC Oxidase, NtPR 1 a/c, E3ligase, and Thaumatin.

* * * * *